(12) United States Patent
Peake et al.

(10) Patent No.: US 8,770,196 B2
(45) Date of Patent: Jul. 8, 2014

(54) SYSTEM AND METHOD FOR TREATING PATIENT WITH OBSTRUCTIVE SLEEP APNEA

(75) Inventors: Gregory Robert Peake, Kingsford (AU); Gregory Scott Smart, Randwick (AU); Robert Edward Henry, Baulkham Hills (AU); Christopher John Baxter, Chatswood (AU)

(73) Assignee: ResMed Limited, Bella Vista (AU)

( * ) Notice: Subject to any disclaimer, the term of this patent is extended or adjusted under 35 U.S.C. 154(b) by 118 days.

(21) Appl. No.: 12/662,602

(22) Filed: Apr. 26, 2010

(65) Prior Publication Data

US 2010/0206313 A1    Aug. 19, 2010

Related U.S. Application Data

(62) Division of application No. 12/010,034, filed on Jan. 18, 2008, now abandoned.

(60) Provisional application No. 60/881,156, filed on Jan. 19, 2007.

(51) Int. Cl.
*A61M 16/06* (2006.01)
*A61F 5/56* (2006.01)

(52) U.S. Cl.
USPC ..................................... 128/207.11; 128/848

(58) Field of Classification Search
USPC .......... 128/845, 848, 200.21, 205.25, 206.21, 128/206.27–207.11, 207.13, 207.29, 128/201.22, 201.23, 201.26, 200.27, 128/201.12, 201.15, 201.17, 202.14, 128/202.16, 202.15, 204.11, 206.16, 863; 433/19, 17, 18, 22
See application file for complete search history.

(56) References Cited

U.S. PATENT DOCUMENTS

| | | | | |
|---|---|---|---|---|
| 3,353,271 | A | 11/1967 | Blechman | |
| 3,528,415 | A * | 9/1970 | Malmin | 128/201.12 |
| 4,382,783 | A | 5/1983 | Rosenberg | |
| 4,739,755 | A * | 4/1988 | White et al. | 128/206.24 |
| 5,954,048 | A | 9/1999 | Thornton | |
| 5,983,892 | A * | 11/1999 | Thornton | 128/201.26 |
| 6,109,265 | A | 8/2000 | Frantz | |
| 6,988,888 | B2 | 1/2006 | Cleary | |
| 2003/0056785 | A1* | 3/2003 | Narihiko et al. | 128/201.26 |
| 2003/0089372 | A1* | 5/2003 | Frater et al. | 128/206.24 |
| 2004/0144391 | A1* | 7/2004 | Brady et al. | 128/848 |
| 2005/0268914 | A1* | 12/2005 | Paoluccio et al. | 128/205.25 |
| 2006/0005840 | A1* | 1/2006 | Cannon | 128/207.11 |
| 2006/0283454 | A1* | 12/2006 | Delaney et al. | 128/206.19 |
| 2007/0209663 | A1* | 9/2007 | Marque et al. | 128/207.11 |

FOREIGN PATENT DOCUMENTS

| WO | WO 01/95965 | 12/2001 |
|---|---|---|
| WO | WO 2007/014429 | 2/2007 |

* cited by examiner

*Primary Examiner* — Patricia Bianco
*Assistant Examiner* — Tarla Patel
(74) *Attorney, Agent, or Firm* — Nixon & Vanderhye P.C.

(57) ABSTRACT

A method for treating obstructive sleep apnea includes providing MAD therapy via an adjustable mandibular advancement device structured to advance the position of the patient's lower jaw, providing CPAP therapy via a mask system structured to deliver a supply of pressurized air to a patient, and selectively adjusting the mask system and/or the mandibular advancement device to alternate and/or balance between CPAP therapy and MAD therapy.

21 Claims, 5 Drawing Sheets

SYSTEM AND METHOD FOR TREATING PATIENT WITH OBSTRUCTIVE SLEEP APNEA

CROSS-REFERENCE TO APPLICATION

This application is a divisional of application Ser. No. 12/010,034, filed Jan. 18, 2008, which claims the benefit of U.S. Provisional Application No. 60/881,156, filed Jan. 19, 2007, each of which is incorporated herein by reference in its entirety.

FIELD OF THE INVENTION

The present invention relates to a system and method for treating a patient with obstructive sleep apnea.

BACKGROUND OF THE INVENTION

Obstructive sleep apnea (OSA) is a common sleep-related respiratory disorder, and many obstructive sleep apnea therapies have been developed to treat the disorder. One such therapy is a mandibular advancement device (MAD) that is used to adjust the position of the patient's lower jaw, e.g., bringing it forward, in an attempt to keep the patient's airway open.

The present invention provides alternative arrangements of MADs to enhance the treatment of OSA.

SUMMARY OF THE INVENTION

One aspect of the present invention relates to a mandibular advancement device including a first anchor provided to one or more of a patient's lower teeth, a second anchor supported at a position spaced from the first anchor, and a biasing arrangement to couple the first and second anchors and provide a biasing force to advance the position of the patient's lower jaw.

Another aspect of the present invention relates to a method for treating obstructive sleep apnea including providing a pillow and positioning the pillow behind the patient's neck to tilt the patient's head back to a position that opens the patient's airway to facilitate breathing.

Another aspect of the present invention relates to a method for treating obstructive sleep apnea including providing a mask system with an air delivery conduit that extends over the patient's head, fitting the mask system to the patient's head, and adjusting the mask system to promote opening of the patient's upper airways.

Another aspect of the present invention relates to a method for treating obstructive sleep apnea including providing MAD therapy via an adjustable mandibular advancement device structured to advance the position of the patient's lower jaw, providing CPAP therapy via a mask system structured to deliver a supply of pressurized air to a patient, and selectively adjusting the mask system and/or the mandibular advancement device to alternate and/or balance between CPAP therapy and MAD therapy.

Another aspect of the present invention relates to a pillow for treating obstructive sleep apnea. The pillow includes a main body adapted to be positioned behind the patient's neck to tilt the patient's head back to a position that opens the patient's airway to facilitate breathing in use.

Another aspect of the present invention relates to a system for treating obstructive sleep apnea. The system includes a mask system adapted to deliver a supply of pressurized air to a patient and an adjustment mechanism provided to the mask system and adapted to promote opening of the patient's upper airways in use.

Another aspect of the present invention relates to a system for treating obstructive sleep apnea. The system includes an adjustable mandibular advancement device to provide MAD therapy, a mask system to provide CPAP therapy, and a control system to selectively adjust the mask system and/or the mandibular advancement device to alternate and/or balance between CPAP therapy and MAD therapy.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
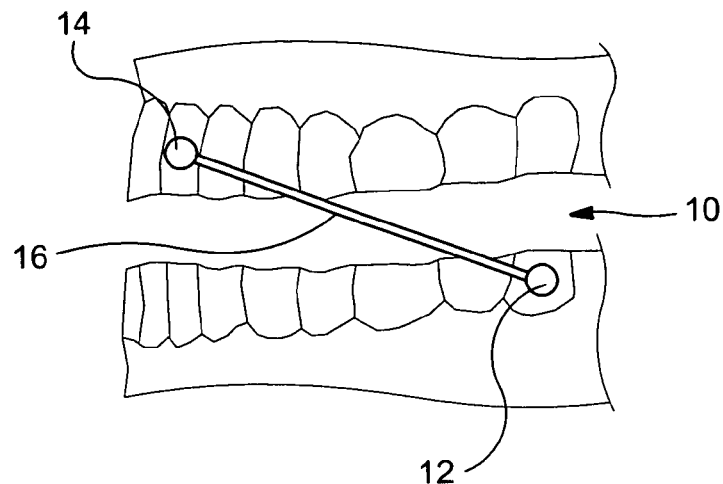
FIG. 1 is a schematic view of a mandibular advancement device including a spring or elastic arrangement according to an embodiment of the present invention.

One aspect of the present invention relates to the way in which a mandibular advancement device may be used in the treatment of obstructive sleep apnea. For example, the mandibular advancement device may be used as a stand-alone device and adjust the position of the patient's lower jaw in an attempt to keep the patient's airway open. Alternatively, the mandibular advancement device may be used in conjunction with a mask system, e.g., nasal mask, full-face mask, nasal and mouth mask, nasal prongs, to enhance the treatment of obstructive sleep apnea. That is, the mandibular advancement device may adjust the position of the patient's lower jaw while the mask system delivers a supply of pressurized air. The mandibular advancement device may be selectively or incrementally adjusted during and/or after a treatment period (e.g., based on apnea severity), and the adjustment of the mandibular advancement device may be coordinated with the mask system (e.g., adjustment coordinated with the pressure level of the mask system).

The following includes descriptions of several embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

1. Mandibular Advancement Device

A mandibular advancement device is structured to advance the position of the patient's lower jaw in an attempt to keep the patient's airway open. For example, the mandibular advancement device may be an internal device that is provided within the patient's mouth, e.g., dental insert, in order to advance the position of the patient's lower jaw. Alternatively, the mandibular advancement device may be an external device that is provided outside the patient's mouth, e.g., engaged with patient's neck and external jaw, in order to advance the position of the patient's lower jaw.

1.1 Internal Device

An "internal" mandibular advancement device includes a portion provided within the patient's mouth to advance the position of the patient's lower jaw. The internal mandibular advancement device may be a fixed device having a fixed magnitude of advancement or an adjustable device having an adjustable magnitude of advancement. Adjustment of the device may be manual and/or automatic, and may be continuously controlled for a patient during changing sleep conditions as needed.

1.1.1 Constant Displacement

Exemplary embodiments of "internal" mandibular advancement devices are disclosed in PCT Application No. PCT/AU2006/001095, filed Aug. 2, 2006, the entirety of which is incorporated herein by reference. In the exemplary embodiments, the mandibular advancement device includes upper and lower members that are fitted to respective upper and lower jaws of the patient. The upper and lower members include flanges (which may be adjustable) that engage one another to advance the position of the patient's lower jaw. Thus, the position of the patient's lower jaw is advanced by a constant displacement.

1.1.2 Constant Force

Instead of constant displacement, constant force may be used to advance the position of the patient's lower jaw. For example, a spring arrangement, an elastic arrangement, and/or a magnetic arrangement may be used to force the position of the patient's lower jaw.

FIG. 1 is a schematic view of a mandibular advancement device including a spring or elastic arrangement 10 according to an embodiment of the present invention. As illustrated, the spring or elastic arrangement 10 includes a lower anchor 12 provided to the patient's lower teeth (e.g., anchor attached to one or more lower teeth), an upper anchor 14 provided to the patient's upper teeth (e.g., anchor attached to one or more upper teeth), and a spring or elastic member 16 (e.g., rubber band) provided or attached between the lower and upper anchors 12, 14. In use, the spring or elastic member 16 provides a biasing force to advance the position of the patient's lower jaw.

Figure 2:
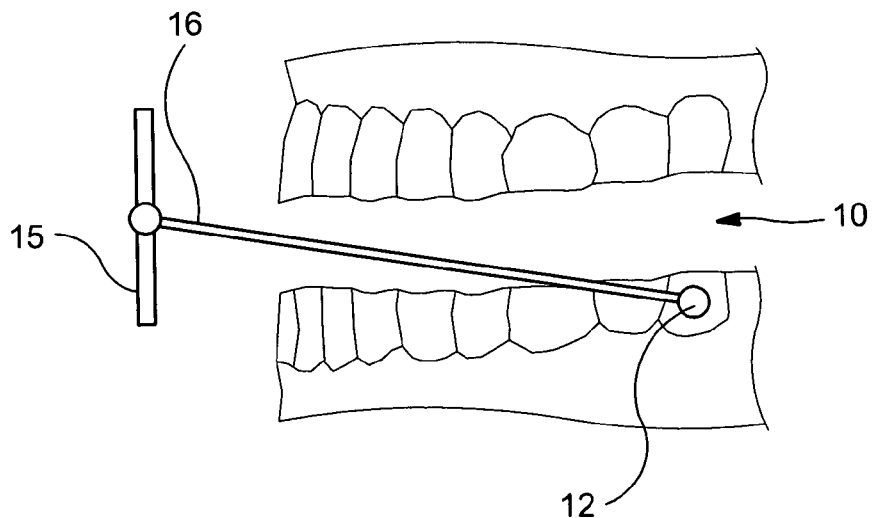
FIG. 2 is a schematic view of a mandibular advancement device including a spring or elastic arrangement according to another embodiment of the present invention.

In an alternative embodiment, as shown in FIG. 2, the spring or elastic arrangement 10 may include a lower anchor 12, an external anchor 15 provided outside the patient's mouth, and a spring or elastic member 16 provided or attached between the lower anchor 12 and the external anchor 15. In use, the spring or elastic member 16 provides a biasing force to advance the position of the patient's lower jaw.

Figure 3:
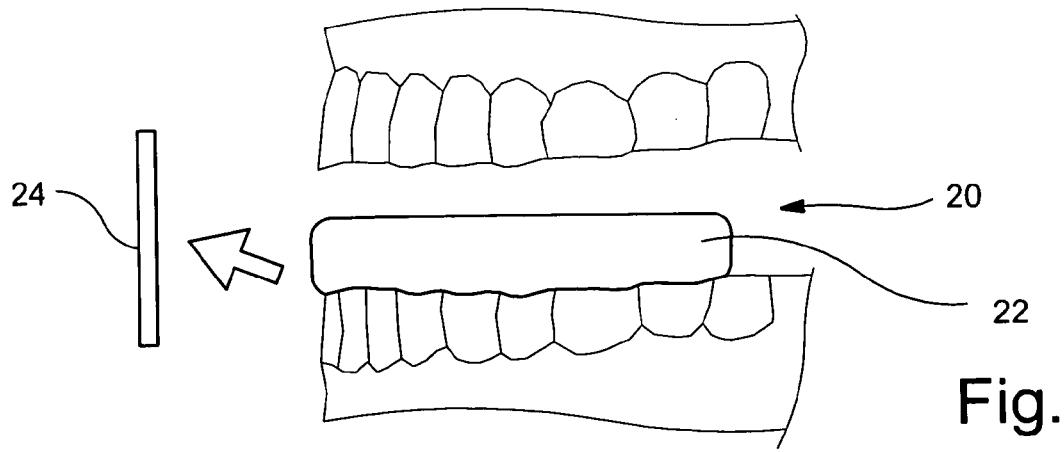
FIG. 3 is a schematic view of a mandibular advancement device including a magnetic arrangement according to an embodiment of the present invention.

FIG. 3 is a schematic view of a mandibular advancement device including a magnetic arrangement 20 according to an embodiment of the present invention. As illustrated, the magnetic arrangement 20 includes a dental insert or mouthpiece 22 provided to the patient's lower teeth and an external device 24 provided outside the patient's mouth. The dental insert 22 is magnetically coupled to the external device such that the external device magnetically "pulls" and/or "pushes" the dental insert 22 and hence the patient's lower jaw outwardly to advance the position of the patient's lower jaw. That is, the magnetic coupling may be provided by magnets with unlike poles that are attracted to one another to "pull" the dental insert outwards at the front of the patient's jaw and/or magnets with like poles that are repelled from one another to "push" the dental insert from behind the patient's jaw. The magnetic arrangement provides an arrangement that is non-invasive and non-mechanical.

An advantage of constant force over constant displacement is that constant displacement may cause a tremendous amount of force on a patient's jaw if the patient's muscles are tight. But, if the muscles are tight, then the patient's oral soft tissue will probably not be blocking the airway, so little to no jaw advancement may actually be necessary.

1.2 External Device

An "external" mandibular advancement device is provided outside the patient's mouth to advance the position of the patient's lower jaw. For example, the "external" mandibular advancement device may engage the patient's head, neck, face, and/or external jaw to advance the position of the patient's lower jaw.

1.2.1 Pillow

Figure 4:
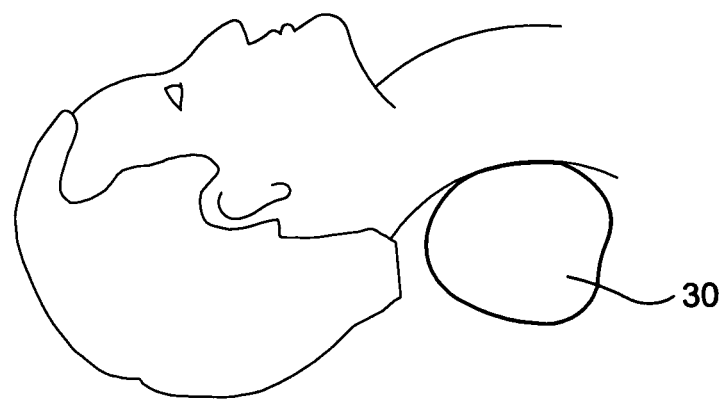
FIG. 4 is a schematic view of a pillow according to an embodiment of the present invention.

In an embodiment, as shown in FIG. 4, the mandibular advancement device may be in the form of a pillow 30 that is positioned, e.g., behind the patient's neck, to tilt the patient's head back. Similar to tilting a patient's head back for administering CPR, the pillow 30 tilts the patient's head back in order to open the patient's airway to facilitate breathing.

Figure 5:
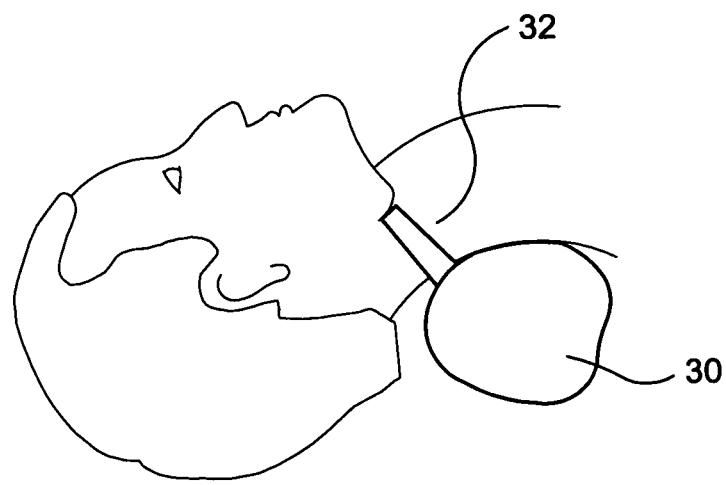
FIG. 5 is a schematic view of a pillow including jaw pushers according to an embodiment of the present invention.

In an alternative embodiment, as shown in FIG. 5, the pillow 30 may incorporate one or more protrusions 32 (e.g., jaw pushers) that are adapted to push up against the back of the patient's jaw in order to advance the position of the patient's lower jaw.

Figure 6:
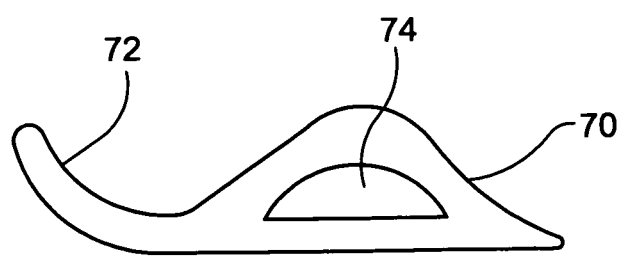
FIG. 6 is a schematic view of a pillow according to another embodiment of the present invention.

In either embodiment, the pillow may have a crescent or wave shape that extends between the shoulders and the base of the patient's skull (e.g., as viewed from the top of the pillow). The pillow can also be formed with an upper portion to effectively cradle the patient's head. For example, FIG. 6 illustrates a pillow 70 having a crescent or wave shape and an upper portion or cradle 72. As illustrated, the pillow 70 may include an inflatable bladder 74 such as that described below in section 1.2.3.

1.2.2 Neck Brace with Jaw Pushers

In an embodiment, the mandibular advancement device may be in the form of a neck brace that includes one or more protrusions or jaw pushers adapted to push up against the back of the patient's jaw in order to advance the position of the patient's lower jaw.

1.2.3 Inflatable Mechanism

In an embodiment, the mandibular advancement device may be in the form of an inflatable mechanism that is adapted to inflate and force the patient to be in a specific position. For example, the inflatable mechanism may be an inflatable pillow that is adapted to inflate and force the patient to tilt his/her head back, roll on his/her side, etc.

1.2.4 Helmet with Mouth Guard

Figure 7:
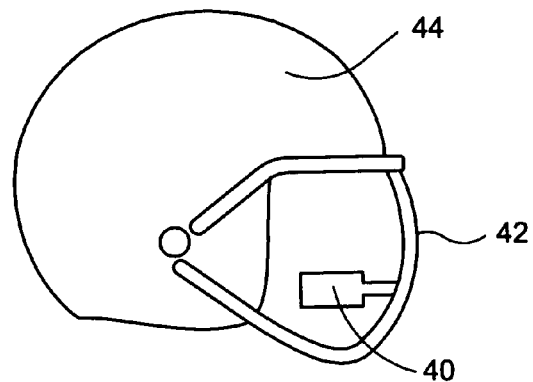
FIG. 7 is a schematic view of a mandibular advancement device incorporating a football-type helmet according to an embodiment of the present invention.

In another embodiment, as shown in FIG. 7, a mouth guard or dental insert 40 may be provided to the patient's lower teeth and coupled with the face mask 42 of a football-type helmet 44 to "pull" the patient's lower jaw forward. The mouth guard 40 may be fixed to the face mask 42 or may include a spring, elastic, and/or a magnetic arrangement with the face mask 42 such as the arrangements described above in section 1.1.2.

2. Mandibular Advancement Device Used in Conjunction with Mask System

In some mask systems, e.g., full-face masks, portions of the mask system may push against the patient's lower jaw which may cause obstructions. An aspect of the present invention relates to a mandibular advancement device used in conjunction with a mask system in order to advance the position of the patient's lower jaw and/or counteract any potential obstructions caused by using the mask system. The mandibular advancement device may be incorporated into any suitable mask system, e.g., full-face, nasal, nasal prongs, mouth mask and nasal prongs, etc.

The mandibular advancement device may be permanently or removably attached to the mask system, e.g., selectively attachable. In an embodiment, the mask system and mandibular advancement device may be formed separately from another and then connected with a lanyard. Also, the mandibular advancement device may be controlled, at least in part, by the mask system, e.g., mask pressure used to operate mandibular advancement device.

In an embodiment, the combination of a CPAP mask system with a mandibular advancement device may allow a reduced CPAP pressure to be used for treatment. For example, a CPAP mask system alone may deliver pressurized gas at about 12 cmH$_2$O for treatment, and a CPAP mask system used with a mandibular advancement device may deliver pressurized gas at about 10 cmH$_2$O for treatment.

2.1 External Clamp

Figure 8:
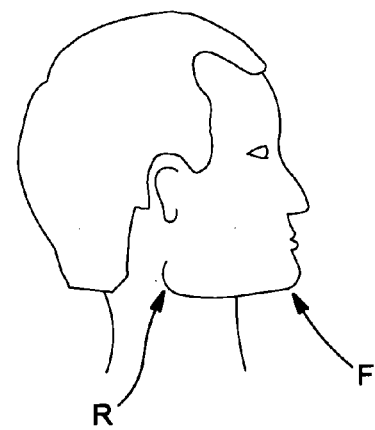
FIG. 8 is a schematic view of clamping locations for a mandibular advancement device according to an embodiment of the present invention.

In an embodiment, the mandibular advancement device may be in the form of an external clamp adapted to clamp or clasp the rear of a patient's jaw (as indicated by arrow R in FIG. 8) or the front of a patient's jaw (as indicated by arrow F in FIG. 8). For example, the external clamp may be coupled to the mask system, e.g., attached to the mask frame and/or mask headgear, and be configured to clamp the rear of a patient's jaw to "push" the patient's chin forward or clamp the front of a patient's jaw to "pull" the patient's chin forward. Preferably, the clamp pushes or pulls outside of the patient's jowls near the temporomandibular joint.

2.2 Tilt Head Back

In an embodiment, the mask system may include a component (e.g., air conduit or delivery tube) that extends over the patient's head, e.g., Adam's Circuit, to promote opening of the patient's upper airways, e.g., by tilting the patient's head back and/or forcing the mask system away from the patient's lower jaw. This prevents the mask system from pushing down against the patient's lower jaw which may cause obstructions.

For example, a mask system including an Adam's Circuit 80 (e.g., a Puritan Bennet Adam™ Interface System) may be provided to a patient's head to tilt the patient's head from a first position (shown in FIG. 9A) to a second position (shown in FIG. 9B) to prevent the mask system from pushing down against the patient's lower jaw and/or to open the patient's airway to facilitate breathing. As illustrated, the Adam's Circuit 80 may tilt the patient's head such that the patient interface (e.g., prongs, cushion, cannula, etc.) translates over a distance d, which may be sufficient to straighten the upper airways, e.g., to thereby clear an occlusion or fold 82 within the patient's airway if the patient's neck is awkwardly angled. In an embodiment, the Adam's Circuit may have a first length that is reduced, e.g., by an adjustment mechanism, to a second length in order to tilt the patient's head from the first position (shown in FIG. 9A) to the second position (shown in FIG. 9B).

Figures 9A, 9B, 9C:
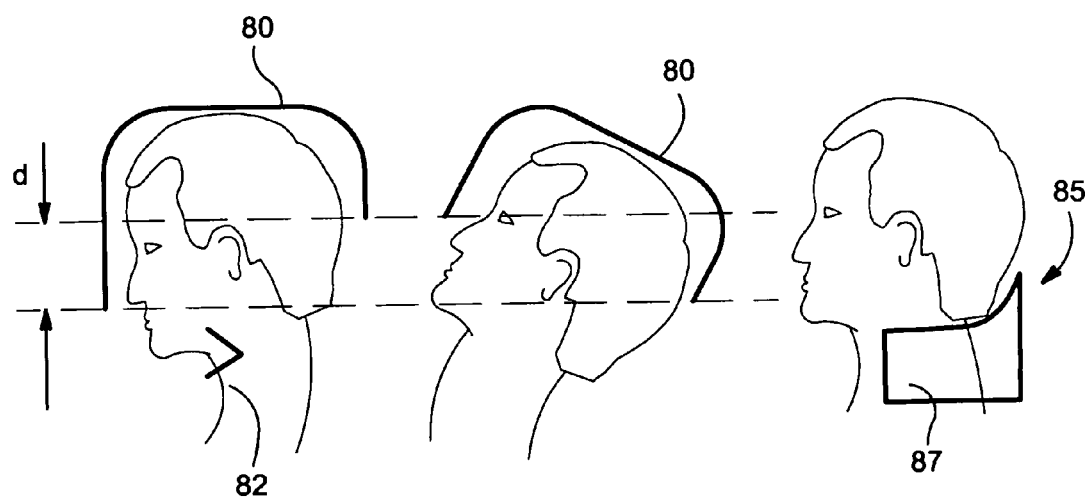
FIGS. 9A and 9B illustrate a mask system including an Adam's Circuit according to an embodiment of the present invention.
FIG. 9C illustrates a half brace according to an embodiment of the present invention.

In another embodiment, the air delivery tube may be movably positionable relative to the headgear. If the patient is slouching and the neck is bent, the tube may be pulled upwardly relative to the patient and the headgear, thus forcing the patient to raise his/her head in order to properly engage the patient interface. In the process, the patient's upper airways are straightened, thus potentially reducing the chances for airway collapse. In this and other embodiments, it may be helpful to provide a fixed reference point on the patient to which the headgear and/or Adam's Circuit are positioned. In one example, the headgear simply has a fairly rigid, depending member braced against the back of the head and the neck and/or shoulders of the patient to maintain the neck at a predetermined angle. In an alternative embodiment, the member could be built into clothes or constitute a separate member (e.g., in a neck brace). For example, FIG. 9C illustrates a half brace 85 that is open in the front of the patient's neck and extends below the patient's jaw line and up behind the back of the patient's head. As illustrated, the brace 85 may include side portions 87 to prevent wobbling of the patient's head in use.

In another embodiment, a mandibular advancement device in the form of a pillow, pillow with jaw pushers, or neck brace with jaw pushers (as described above) may be provided to tilt the patient's head back.

2.3 Facial Support

In embodiments, the mask system may be supported by portions of the patient's face to prevent the mask system from pushing down against the patient's lower jaw. For example, the mask system may clamp onto sides of the patient's midbridge, e.g., like a G-clamp, or use the patient's ears as support.

2.4 Inflatable Mechanism

As noted above, the mandibular advancement device may be in the form of an inflatable mechanism that is adapted to inflate and force the patient to be in a specific position. In an embodiment, the inflatable mechanism may be incorporated into the headgear of the mask system. For example, the headgear may include an inflatable portion or bladder that is adapted to inflate and force the patient to tilt his/her head, roll on his/her side, roll over, etc. The pressure to inflate the bladder may be provided by the flow generator of the mask system.

2.5 Magnetic Arrangement

As noted above, a magnetic arrangement may be provided to "pull" and/or "push" the patient's lower jaw. In an embodiment, the mask, e.g., full-face mask, may be magnetically coupled to the headgear such that the headgear magnetically "pulls" and/or "pushes" the mask to adjust the position of the patient's lower jaw, e.g., mask provided with magnetic attraction and headgear provided with magnetic repulsion.

2.5.1 Electromagnetic Arrangement

In an alternative embodiment, an electromagnetic arrangement may be provided for force advancement of the patient's lower jaw. The electromagnetic arrangement may include a permanent magnet, e.g., provided to the mask, and an electromagnet, e.g., provide to the headgear, to allow the headgear to "pull" and/or "push" the mask to adjust the position of the patient's lower jaw. The electromagnet allows adjustment of the force.

2.6 Updated Mask Structure

The mask, e.g., full-face mask, may include structure to allow movement and/or counteract any potential obstructions to movement of the patient's lower jaw.

Figure 10A:
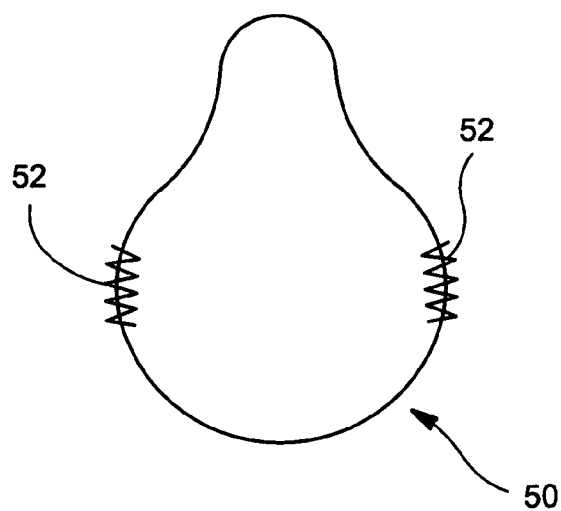
FIGS. 10A and 10B are schematic views of a mask including a pivotally mounted lower section according to an embodiment of the present invention.
Figure 10B:
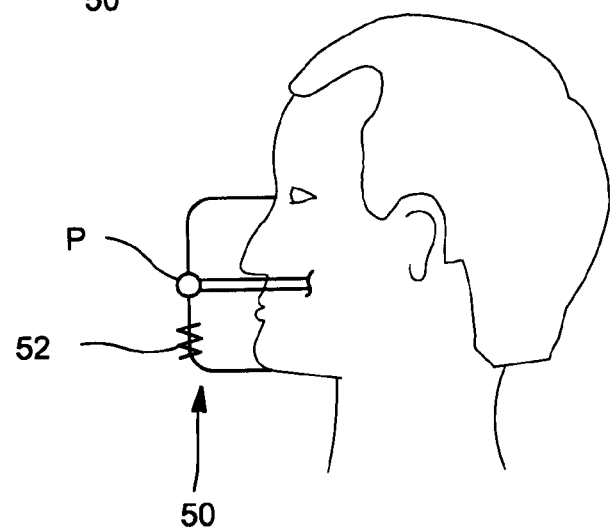

For example, the lower jaw region of a full-face mask may be structured to allow movement of the patient's lower jaw. In an embodiment, as shown in FIGS. 10A and 10B, the mask may include a pivotally mounted lower section 50 to allow movement of the patient's lower jaw in use. The lower section 50 may be spring biased. For example, the lower section 50 may incorporate one or more springs 52, with the attachment points P for headgear straps positioned above the springs 52. The springs 52 may be arranged to bias the lower section 50 towards the patient's face to provide a sealing force but allow sufficient movement of the patient's lower jaw in use. Alternatively, the springs 52 may be arranged to bias the lower section 50 away the patient's face to allow sufficient movement of the patient's lower jaw in use.

Figure 11:
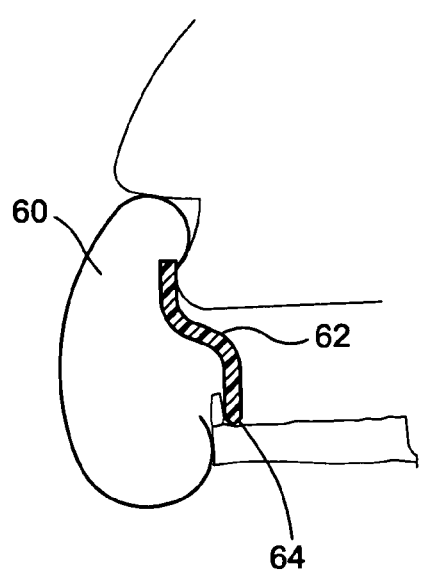
FIG. 11 is a schematic view of a mask including a portion that extends into the patient's mouth according to an embodiment of the present invention.

In another exemplary embodiment, as shown in FIG. 11, a mask 60, e.g., mouth mask, may support a portion 62 that extends into the patient's mouth and provides a distal end 64 adapted to engage the patient's lower jaw and/or lower teeth to push the patient's lower jaw forward. As illustrated, the portion 62 has no contact with the upper jaw and/or upper teeth of the patient in use. In an embodiment, the portion 62 may be supported by a frame of the mask.

In another embodiment, a mouth guard or dental insert may be provided to the patient's lower teeth and coupled with the back of the patient's head and/or headgear of the mask system to "push" or "pull" the patient's lower jaw forward.

In another embodiment, a portion of the pressurized gas may be used to force the patient's lower jaw forward, e.g., inflatable bladder to force patient's lower jaw forward.

2.7 Coordinated with Mask Pressure Level

In an embodiment, displacement provided by the mandibular advancement device may be coordinated with the pressure level of the mask system. That is, a control system may be provided to alternate and/or balance between CPAP therapy provided by the mask system and MAD therapy provided by the mandibular advancement device.

For example, a pressure level of 12 cmH$_2$O provided by the mask system may be suitable with 8 mm of advancement provided by the mandibular advancement device, and a pressure level of 20 cmH$_2$O provided by the mask system may be suitable with 12 mm of advancement provided by the mandibular advancement device. However, other suitable relations between the pressure level and MAD setting may be provided, e.g., depending on the patient and/or required treatment. It should be appreciated that controlling the alternation and/or balance may be manual and/or automatic, e.g., automatically changed during the night.

Figure 12:
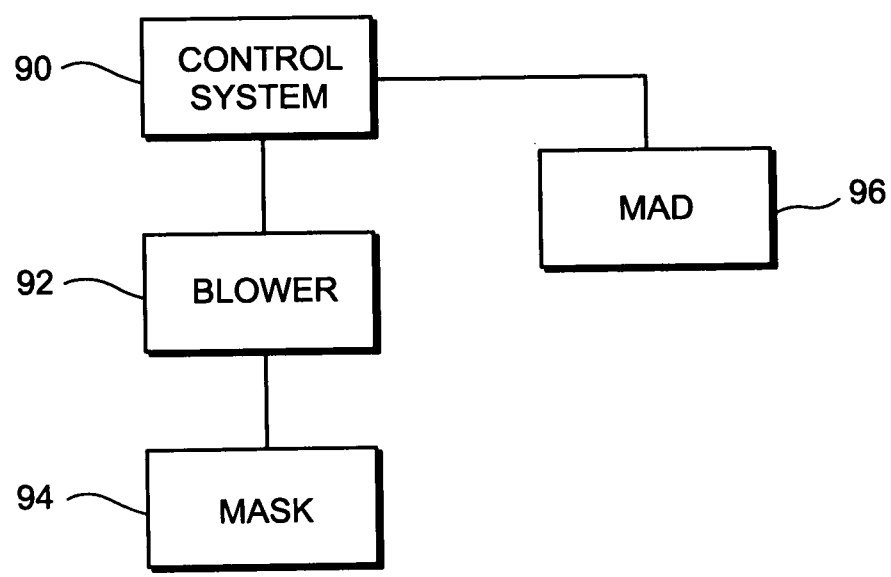
FIG. 12 is a schematic view of a control system to alternate the balance between CPAP and MAD therapy according to an embodiment of the present invention.

FIG. 12 is a schematic view of a control system to alternate and/or balance between CPAP and MAD therapy. As illustrated, the control system 90 is communicated with blower 92 to control and/or receive feedback regarding the delivery of pressurized air to mask 94 for CPAP therapy. The control system 90 is also communicated with MAD 96 to control and/or receive feedback regarding MAD therapy. Based on the patient and/or required treatment, the control system 90 may automatically update and/or recommend suggested settings to alternate and/or balance between CPAP therapy provided by the mask system and MAD therapy provided by the MAD.

3.0 Improvements to Prior Art Masks

One or more of the above-described embodiments of mandibular advancement devices may be adapted for use and/or incorporated into the masks described in PCT Publication WO 01/95965, which is incorporated herein by reference in its entirety. For example, an inflatable mechanism, e.g., inflatable pillow, may be adapted for use with the disclosed masks.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike.

What is claimed is:

1. A method for treating obstructive sleep apnea, comprising:
   providing a mask system with an air delivery conduit that extends over the patient's head;
   fitting the mask system to the patient's head;
   adjusting the mask system to promote opening of the patient's upper airways; and
   adjusting the position of the mask system to cause the angle of the patient's neck to change.

2. The method according to claim 1, wherein adjusting the mask system includes adjusting the mask system to tilt the patient's head back.

3. The method according to claim 2, further comprising reducing the length of the air delivery conduit that extends over the patient's head to tilt the patient's head back.

4. The method according to claim 1, wherein adjusting the mask system includes forcing the mask system away from the patient's lower jaw.

5. The method according to claim 1, further comprising raising the mask system to cause the upper airway to open.

6. A system for treating obstructive sleep apnea, comprising:
   a mask system adapted to deliver a supply of pressurized air to a patient; and
   a mechanism provided to the mask system that promotes opening of the patient's upper airways in use wherein the mechanism is structured to adjust the position of the mask system to cause the angle of the patient's neck to change.

7. The system according to claim 6, wherein the mask system includes a nasal mask, full-face mask, nasal and mouth mask, and/or nasal prongs.

8. The system according to claim 6, wherein the mask system includes an air delivery conduit that, in use, extends over the patient's head.

9. The system according to claim 8, wherein the mechanism is coupled to the air delivery conduit, the mechanism structured to reduce the length of the air delivery conduit to, in use, tilt the patient's head back.

10. The system according to claim 6, wherein the mechanism is structured to adjust the mask system to, in use, tilt the patient's head back.

11. The system according to claim 6, wherein the mechanism is structured force the mask system away from the patient's lower jaw.

12. The system according to claim 6, wherein the mechanism is structured to raise the mask system to cause the upper airway to open.

13. A full-face mask system for use in respiratory therapy, comprising:
   an upper region configured to cover at least the patient's nose;
   a lower region pivotably connected to the upper region and proximal to the patient's lower jaw; and
   a biasing mechanism positioned at a pivot point of the lower region,
   wherein the biasing mechanism is constructed and arranged to bias the lower region into sealing engagement with the patient's face.

14. A full-face mask system according to claim 13, wherein the biasing mechanism is positioned below a headgear attachment region.

15. A full-face mask system according to claim 13, wherein the biasing mechanism includes a spring.

16. A full-face mask system according to claim 13, wherein the biasing mechanism includes more than one spring.

17. A full-face mask system according to claim 13, wherein the biasing mechanism is constructed and arranged to bias the lower region against the patient's face.

18. A full-face mask system according to claim 13, wherein the pivot point is located between the upper and lower regions.

19. A full-face mask system for use in respiratory therapy, comprising:
   an upper region;
   a lower region proximal to the patient's lower jaw and configured to sealingly engage around the patient's mouth, the lower region being pivotably mounted with respect to the upper region to allow movement of the patient's lower jaw; and
   a biasing mechanism constructed and configured to pivot the lower region with respect to the upper region.

20. A full-face mask system according to claim 19, wherein the upper region is configured to sealingly engage with the patient's face.

21. A full-face mask system according to claim 19, wherein the biasing mechanism is configured to bias the lower section away from the patient's face.

* * * * *